United States Patent [19]
Doglio et al.

[11] Patent Number: 5,837,503
[45] Date of Patent: Nov. 17, 1998

[54] VECTOR CONTAINING VIRAL GENE TRANSCRIBED BY RNA POLYMERASE III AND METHODS FOR USE

[75] Inventors: Alain Doglio, St Andre; Jean-Claude Lefebvre, Drap; Laurence Cagnon, Nice, all of France

[73] Assignee: Universite de Nice-Sophia-Antipolis, Nice, France

[21] Appl. No.: 661,893

[22] Filed: Jun. 12, 1996

Related U.S. Application Data

[63] Continuation of Ser. No. 87,054, Jul. 7, 1993, abandoned.

[51] Int. Cl.$^6$ .............................. C12P 19/34; C12N 15/86
[52] U.S. Cl. ...................................... 435/91.31; 435/91.33; 435/91.4; 435/91.42; 435/91.51; 435/320.1
[58] Field of Search ................................ 435/69.1, 172.3, 435/240.2, 320.1, 172.1, 91.1, 91.3, 91.31, 91.32, 91.33, 91.4, 91.41, 91.42, 91.52; 536/23.1, 23.72, 24.1

[56] References Cited

FOREIGN PATENT DOCUMENTS 0 387 775  9/1990  European Pat. Off. .

OTHER PUBLICATIONS

Miller et al., "Improved Retroviral Vectors for Gene Transfer and Expression", BioTechniques, vol. 7, No. 9, 1989, pp. 980–990.

Stratford–Perricaudet et al., "Gene Transfer into Animals: The Promise of Adenovirus", Human Gene Transfer, vol. 219, 1991, pp. 51–61.

Cotten et al. "Ribozyme Mediated Destruction of RNA in vivo", EMBO J., vol. 8, No. 12, pp. 3861–3866, 1989.

Ghadge et al. "Binding of the Adenovirus VAI RNA to the Interferon–Induced 68–kDa Protein Kinase Correlates with Function", PNAS, vol. 88, pp. 7140–7144, Aug. 1991.

Jennings et al. "Inhibition of SV40 Replicon Function by Engineered Antisense RNA Transcribed by RNA Polymerase III", EMBO J., vol. 6, No. 10, pp. 3043–3047, 1987.

*Primary Examiner*—David Guzo
*Attorney, Agent, or Firm*—Finnegan, Henderson, Farabow, Garrett & Dunner, L.L.P.

[57] ABSTRACT

A recombinant vector containing a cassette for transcription by RNA polymerase III is disclosed. The cassette contains a viral gene transcribed by RNA polymerase III into which an oligonucleotide, a DNA fragment, has been inserted between or outside the boxes A and B constituting the promoter of the viral gene is provided. A method for the intracellular production of an RNA fragment in vitro or in vivo, in which eukaryotic cells containing RNA polymerase III are transfected or infected with a vector according to the invention, containing as oligonucleotides a DNA fragment corresponding to the reverse transcript of the RNA, and in which the eukaryotic cells thus transfected or infected are cultured in a suitable culture medium is also provided. The use of the vectors as a medicinal product is further provided.

29 Claims, 11 Drawing Sheets

FIG.1

ADENOVIRUS 2 VAI Gene

```
         10569      10579      10589      10599      10609
    CGTGCGCAGT CGTTGACGCT CTAGACCGTG CAAAAGGAGA GCCTGTAAGC 10619      10629      10639      10649      10659
    GGGCACTCTT CCGTGGTCTG GTGGATAAAT TCGCAAGGGT ATCATGGCGG
                    BOX A 10669      10679      10689      10699      10709
    ACGACCGGGG TTCGAACCCC GGATCCGGCC GTCCGCCGTG ATCCATGCGG
                  BOX B 10719      10729      10739      10749      10759
    TTACCGCCCG CGTGTCGAAC CCAGGTGTGC GACGTCAGAC AACGGGGAG 10769      10779      10789      10799      10809
    CGCTCCTTTT GGCTTCCTTC CAGGCGCGGC GGCTGCTGCG CTAGCTTTTT

10819
    TGGCCACTGG
``` antisense and "random" sequences inserted at nucleotide 10711 of the VAI gene.

anti-Tat  TGC TCT CCT CTG TCG AGT AAA GAC AGG ATA anti-Rev  TCG TCG CTG TCT CCG CTT CTT CCT GCC A Random   TGC TCT TGT CCC GTC ATC GTT GCC CCT C

5'  ATC CAT GCG GTT ACC GCC CGC GTG  3'
              10711

VAI gene

Urea/acrylamide gel analysis of the products of acellular transcription of the PVV2/VAI/antisense constructions
Expected sizes:
VAI RNA: 160 bp
anti-rev VAI RNA: 168 bp
anti-tat VAI RNA: 190 bp

FIG_4

"anti-tat": AS1, AS2, AS6, AS7, AS8.
"anti-rev": AS3, AS4, AS9, AS10, AS12.
CEM: positive control of infection

FIG_5 insertion site
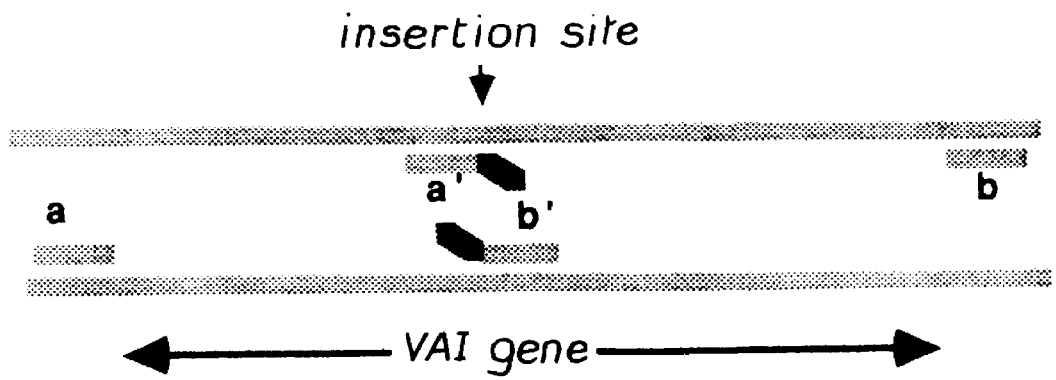
VAI gene
First two separate "half-amplifications": a and a', b and b':
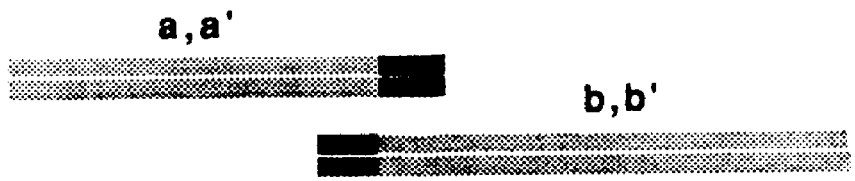
Mixing of the first two half-amplifications and further amplification with a and b:
exogenous sequence inserted
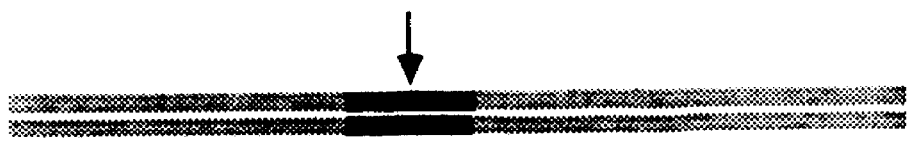
FIG_7

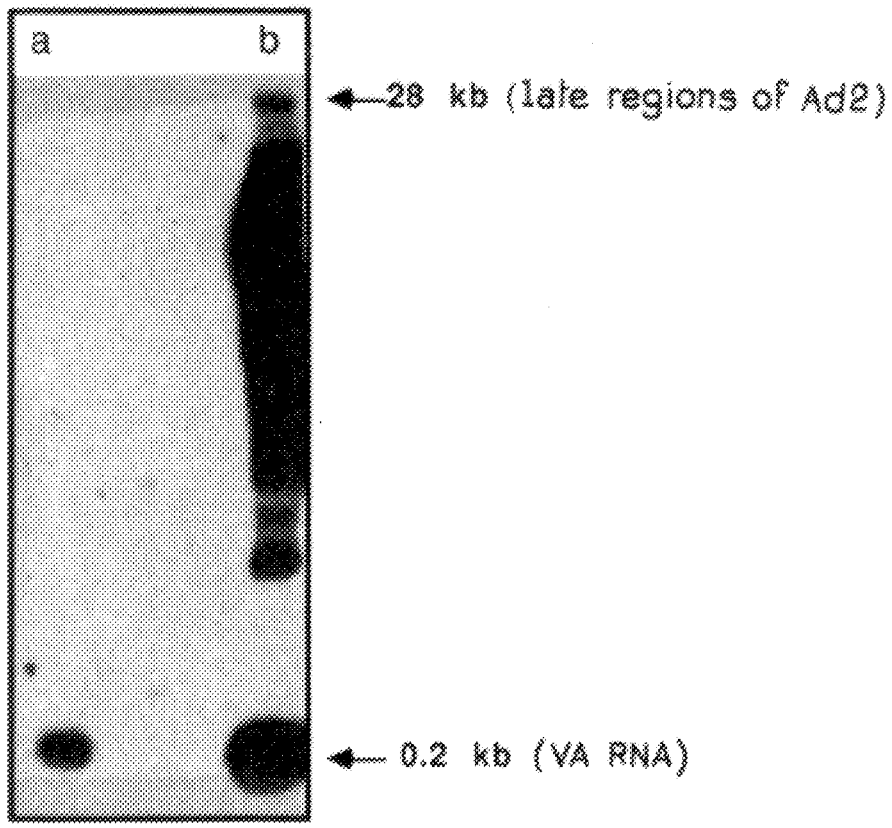
a: RNA of AS10 cells expressing the VA/anti-rev construction
b: RNA of HepG2 cells infected with adenovirus 2
FIG_8

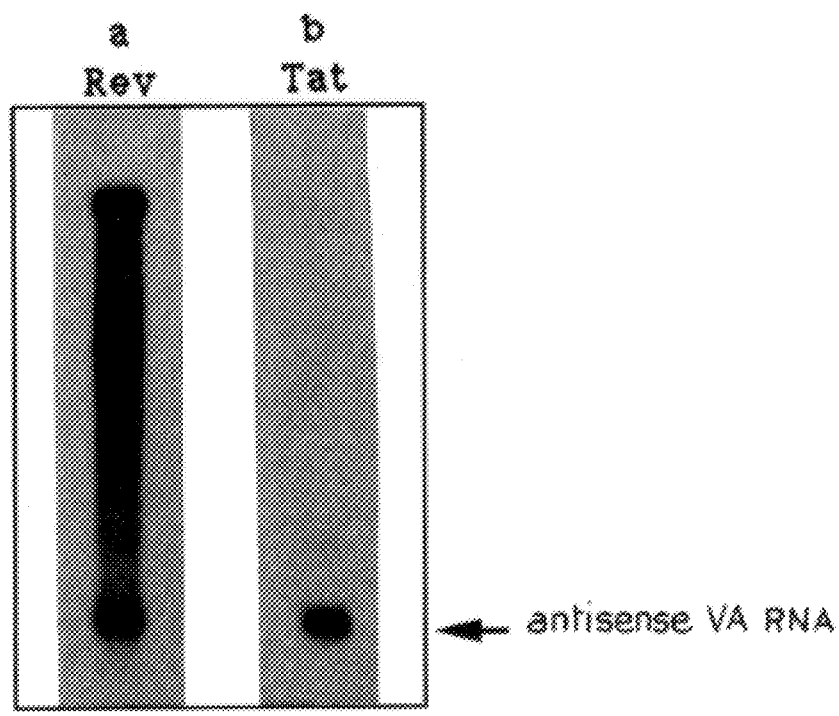
FIG_9

A- Vector I:
- derived from pMV7:
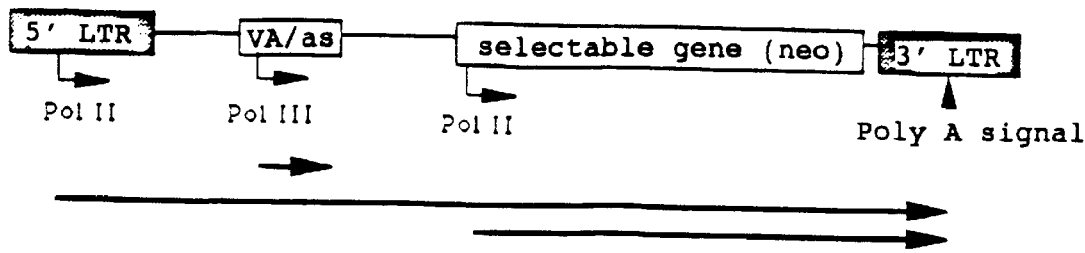
B- Vector II:
- pMV7 from which the enhancer regions have been deleted and replaced by the VA-antisense gene or genes.
- the selectable gene may or may not be present.
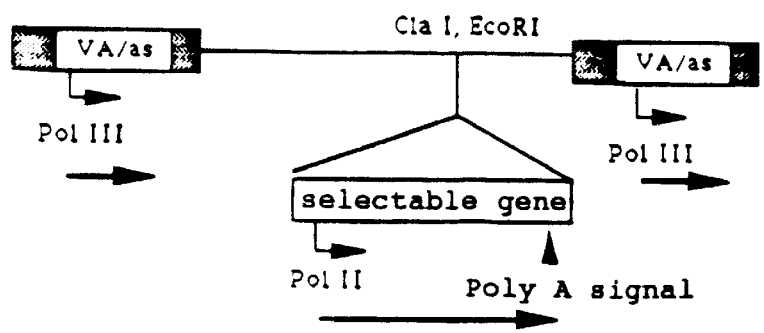
Legend:
→ RNA transcribed from the various promoters
▓ LTR
☐ selectable gene
VA/as VA-antisense gene
FIG. 10

VECTOR CONTAINING VIRAL GENE TRANSCRIBED BY RNA POLYMERASE III AND METHODS FOR USE

This application is a continuation of application Ser. No. 08/087,054, filed Jul. 7, 1993, now abandoned.

The present invention relates to recombinant DNA vectors, in particular of the plasmid or viral type, containing a cassette for transcription by RNA polymerase III, consisting of a viral gene naturally transcribed by RNA polymerase III.

The present invention also relates to eukaryotic cells transfected or infected with vectors according to the invention.

The present invention also relates to a method for the intracellular production of an RNA fragment in vitro or in vivo, by culturing eukaryotic cells transfected or infected with the vectors according to the invention.

The present invention also relates to the use of vectors according to the invention as a medicinal product.

Antisense molecules are RNA sequences which hybridize selectively with the messenger RNAs to which they are complementary, and thereby block the expression of the gene in question (maturation of the RNA, translation). Work carried out since the beginning of the 1980s testifies to the efficacy of such a system for repressing many cell or viral functions (1,2).

The prospects for potential applications of these antisense molecules are considerably in basic research. Use may be made of antisense molecules to correct the expression of certain "abnormal" phenotypes or to combat effectively viruses for which the traditional approaches (vaccination, chemotherapy, etc.) prove intricate, as is the case with human immunodeficiency virus (HIV).

One of the problems created by the use of antisense molecules lies in the fact that these molecules are effective at high intracellular concentrations, very much higher than those of their substrate. Since the intracellular concentration of antisense molecules is the outcome of the difference between synthesis and degradation, approaches that favor the synthesis and stability of the products formed have been sought according to the invention. From this viewpoint, the efficacy of functioning of the antisense molecule with respect to its target is an important parameter since, the more "potent" a molecule, the less it will require a high concentration to obtain a maximum effect.

In eukaryotes, RNA polymerase III is the enzyme responsible for the synthesis of a wide variety of small cytoplasmic or nuclear RNAs. The main representatives are transfer RNAs (tRNA) or type 5S ribosomal RNAs (3).

RNA polymerase III is capable of transcribing cloned DNA fragments effectively in an acellular system. This is possible on condition that these DNA fragments contain the promoter regions specific to transcription by polymerase III. These promoter regions are now well characterized (4), and consist first and foremost of discontinuously arranged intragenic regions. In the case of tRNA type genes, two DNA regions are involved: "box A" and "box B", each one composed of 11 nucleotides (consensus sequence) and spaced apart by an intermediate region of variable size (4).

The RNAs transcribed by polymerase III are noteworthy for their small size and most particularly for their spatial conformation. Thus, the clover-leaf structure of tRNAs is especially well known. This secondary structure probably provides tRNAs with stability, but most particularly with functionality. The sequences present in the loops (anticodon) are free to hybridize with a complementary RNA. Cotten and Birnstiel in 1989 (5) proposed inserting a "ribozyme/antisense" sequence into the tRNA$^{met}$ gene of Xenopus. The oligonucleotide was inserted into the intermediate region situated between box A and box B of the promoter regions so as to be correctly presented in the anticondon (ribtRNA$^{met}$, Reference 2).

Some viruses (adenovirus, Epstein-Barr virus, herpesvirus) are equipped with genes transcribed by RNA polymerase III. In particular, adenoviruses are equipped with two similarly organized genes referred to as VAI and VAII (VA: virus-associated) coding for two different VA RNAs, VAI RNA and VAII RNA (6). The VA genes are naturally cloned and functional in the adenovirus genome. More than 10$^7$ VA RNA molecules are found in a cell infected with an adenovirus. These small RNAs, containing 150 nucleotides, are transcribed from a promoter containing two separate regions (box A and box B) located in the L1 region of the adenovirus genome (7). The VA RNAs exert an effect on translation: adenovirus mutants defective in VAI RNA express their messenger RNAs normally but are incapable of accomplishing their translation effectively. The explanation of this phenomenon is that the interferon-induced protein kinase DAI is inhibited by the VAI RNA, thereby enabling its substrate eIF-2 to elude phosphorylation and hence inactivation (9) (the eIF-2 factor being necessary for initiation of translation). The interaction between VAI RNA and the kinase has been well documented (10, 11). Two separate regions of the RNA have been described, one being involved in the binding of the RNA to the DAI protein (nucleotides 93 to 136) and the other in the inhibition of the kinase activity (nucleotides 54 to 77).

Jennings and Molloy (12) have shown that it was possible to represent the expression of an SV40 virus replicon in COS1 cells by means of a 163-bp anti-SV40 antisense RNA (T antigen) grafted at the 3' end of the VAI gene. After transfection of the COS1 cells by various constructions (sense, antisense), the authors show on a transitory expression system that the T antigen is 50% repressed.

According to the present invention, a short antisense sequence has been inserted within the VA gene with the object of obtaining a functional assembly, that is to say one which preserves the partially double-stranded structure of the VA gene and its loop conformation, of the hairpin type, which interacts with the protein kinase. This maintenance of the structural topology results in greater intracellular stability on the one hand and preservation of the functionality of the VA gene on the other hand.

It has, in effect, according to the present invention, been discovered that the exceptional efficacy of functioning of these small RNAs in their role of inhibition of protein kinase DAI activity may be utilized by diverting it from its primary mission and directing it towards another target making use of antisense molecules or ribozymes. According to the invention, these VA genes are hence used as a shuttle system, especially for the development of a new family of antisense RNA molecules expressed in eukaryotes and potentially usable for a wide range of applications.

According to the present invention, a "cassette" gene model has been developed, permitting the ready insertion of antisense oligonucleotides or ribozymes into the VA gene without affecting its level of transcription, and it has been possible to measure the relative efficacy of these constructions in respect of inhibition of replication of the HIV virus in culture. The present invention is based, in effect, on the use of RNA polymerase III for transcribing effectively cloned genes (VAI) carrying antisense sequences or ribozymes (in the form of small-sized—15 to 25 nucleotides—exogenous DNA fragments inserted into the gene in question).

In its most general aspect, the subject of the present invention is a recombinant DNA vector containing a cassette for transcription by RNA polymerase III, consisting of a viral gene transcribed by RNA polymerase III into which an oligonucleotide, a DNA fragment, has been inserted between or outside the boxes A and B constituting the promoter of said viral gene.

The level of transcription of the VA genes by polymerase III is very high. This enzyme is well conserved in most eukaryotes and is, as a result, adaptable to many cell or animal models; the ubiquitous representation of this enzyme in all tissues gives rise to no tissue-specific limitation.

The use of these stable and functional viral genes transcribed in large amounts hence makes them especially effective in situ RNA production systems.

The organization of the genes transcribed by this enzyme is advantageous on account of the absence of regulatory DNA sequences in an "extragenic" position, thereby simplifying the scheme of regulation of transcription and providing for compaction of the genetic information. The intragenic position of the promoters avoids having to manipulate untranscribed regions, thereby enabling small, easily cloned genes to be manipulated. Lastly, the viral genes according to the invention, such as VA, afford numerous possibilities of insertion of oligonucleotides without affecting their level of transcription and the secondary structure of the RNA transcribed.

In a suitable embodiment, the viral gene is an adenovirus VA gene, or an Epstein-Barr virus EBR gene, or a viral gene transcribed by a herpesvirus RNA polymerase III.

In particular, an adenovirus, particularly adenovirus 2, VAI or VAII gene may be mentioned.

The adenovirus VAI gene was chosen as a pilot system, as an example of implementation of the invention, since it is especially well described in the literature. However, all viral genes similar to VAI and transcribed by RNA polymerase III can be suitable as well.

As a suitable vector according to the invention, a plasmidial or episomal replicative vector or a viral vector may be mentioned.

In particular, an episomal vector carrying the origin of replication of the Epstein-Barr virus (oriP) as well as the sequences coding for the EBNA-1 protein will be used.

As regards the choice of vector, it is, in effect, preferable to stay as close as possible to the "natural" system, disturbing it as little as possible. For this reason, it is preferable to use an autonomously replicating vector (episome). The use of an episomally replicating vector can be a good means for expressing antisense molecules in eukaryotic cells, and most especially in T lymphocytes. The cloning of VA/antisense genes into vectors which replicate in episomal form in a eukaryotic system is especially suitable. These vectors carry the origin of replication of the Epstein-Barr virus (oriP), as well as sequences coding for the Ebnal protein which is strictly necessary for replication of the DNA molecule carrying oriP.

A greater efficacy of functioning of polymerase III is noted on episomes, together with a stimulation of transcriptional activity in the presence of the E1a protein. These properties are turned to good account to improve the proposed system.

The viral vector according to the invention is preferably a DNA virus, but can also be an RNA retroviral vector; it will then contain the RNA transcript of the transcription cassette according to the invention. In view of the fact that infection of a cell with a retrovirus leads to the production of a circularized proviral DNA, this proviral DNA is the species which will, in turn, be transcribed by the RNA polymerase III according to the invention, this not ruling out the functioning of the genetic construction used once the retroviral DNA is integrated.

In a suitable embodiment according to the invention, the oligonucleotide is inserted into the intermediate regions situated between boxes A and B of the VA gene.

For a therapeutic application, the VA gene is preferably inactivated as regards inhibition of interferon action, by deletion or mutation in the VA gene of the sequence elements which are critical for inactivation of the interferon-induced protein kinase DAI.

This inactivation may be carried out by direct insertion of the oligonucleotide into the regions responsible for the activity of inhibition of interferon action, a region described as being in the adenovirus 2 VAI gene between and including nucleotides 10672 and 10745. By this expedient also, the affinity of the oligonucleotide for the target sequence is optimized on account of the spatial topology of this region in the form of a loop.

The integrity of the central region of the VA gene of nucleotides 10694 to 10730 (loop IV) is, in effect, critical for maintaining the inhibitory activity of the VA RNA with respect to P68 kinase. This region is situated outside the regulatory zones (boxes A and B), and its deletion does not affect the transcription of the VA gene.

According to a first embodiment of the present invention, the natural activity of the adenovirus 2 VAI gene is inactivated by insertion of the antisense molecule into the central region of nucleotides 10694 to 10730, and more especially 10702 to 10728, or in place of this region which has been deleted.

However, in order to be able to construct chimeric VA-antisense genes for which the antisense molecule is introduced outside this region, in another embodiment, a VA gene from which the central region (nucleotides 10702 to 10728) has been deleted in constructed. In practice, "overlap" PCR (FIG. 7) enables these deletions to be carried out when the oligonucleotides a' and b' are spaced apart from the region to be deleted. Furthermore, a new restriction side (EcoRV; GATATC) may be created, in particular, by the juxtaposition of the two ends flanking the deletion (GAT and ACC) by means of the mutation of nucleotide 10729 (ACC replaced by ATC). This additional site may be used subsequently for the cloning of antisense or ribozymic sequences in place of the deleted loop IV. This gene is referred to as VA delta IV.

Apart from the newly created EcoRV site, other regions of the VA gene may be used as sites for insertion of exogenous sequences (by overlap PCR), especially the regions corresponding to the single-stranded loops of the VA RNA.

The insertion of exogenous antisense sequences into one of these regions or in place of one of these regions, the region being deleted, enables the added oligonucleotides to appear on the secondary structure as "extrusions" relative to the principal axis of the VA RNA. As a result, they are accessible to sense RNAs. There may be mentioned chiefly, from 5' to 3', the following single-stranded regions:

loop I, nucleotides from 10635 to 10639 (-TAAAT-), situated between boxes A and B, loop III, nucleotides from 10682 to 10688 (-ATCCGGC-), situated after box B, loop V, nucleotides from 10733 to 10736 (-GGTG-).

Moreover, the terminal end of the VA delta IV gene may also be used as an insertion site. The added sequences are then placed immediately upstream of the stop sequence (-TTTT-) and define an extension with respect to the VA molecule. The single Eco47III site (-AGC/GCT) from nucleotides 10758 to 10763 may be used for this purpose.

In a particular embodiment, the oligonucleotide is inserted at nucleotide 10711 of the adenovirus 2 VAI gene shown in FIG. 1.

Preferably, the oligonucleotide according to the invention contains from 15 to 40 nucleotides, and as a further preference 15 to 25.

In the context of a therapeutic application, the oligonucleotide may correspond to an antisense RNA molecule or to a ribozymic RNA structure.

With the object of improving the efficacy of hybridization between the antisense RNA molecule and its substrate, many studies are currently directed towards the search for target sequences correctly defined in terms of hybridization parameters (affinity, accessibility).

Ribozymic sequences (25) are minimum consensus sequences required for an RNA molecule to be capable of hydrolyzing another RNA molecule according to a catalytic mode. These ribonucleotides having catalytic activity (ribozymes) are capable of cleaving a target RNA with which they are hybridized in a specific manner (as a result of two sequences of 15 nucleotides complementary to the target RNA and placed on each side of the catalytic sequence). These ribozymic sequences, comparable to "super antisense" sequences, may be used profitably in our system, increasing the functional efficacy of the whole.

Moreover, the VA gene is small in size (160 nucleotides for adenovirus 2 VAI). This makes it possible, according to the present invention, to use simultaneously several VA-antisense genes carried by the same genetic construction. The object in view is to define antisense "cocktails" (for example, in the case of HIV, concomitant use of three different genes: anti-rev, anti-tat and anti-encapsidation signal). These multiple genetic constructions afford two substantial advantages:

additivity of the genes and hence increase in the intracellular concentration of the antisense RNAs, multiplicity of the target sequences and hence greater efficacy of functioning.

Furthermore, in the case of viruses endowed with considerable genetic variability and which "adapt" to the treatment used, recourse to the use of several antisense sequences enables the emergence of genetic variants to be avoided.

The subject of the present invention is hence also a vector containing several identical or different viral genes transcribed by RNA polymerase III, into which an identical or different oligonucleotide has been inserted outside the boxes A and B of each of said viral genes.

The subject of the present invention is also a method for the intracellular production of an RNA fragment in vitro or in vivo, in which eukaryotic cells containing RNA polymerase III are transfected or infected with a replicative vector according to the invention, containing as oligonucleotide a DNA fragment corresponding to the reverse transcript of said RNA, and in which the eukaryotic cells thus transfected or infected are cultured in a suitable culture medium.

The subject of the present invention is, in addition, as seen, the use as a medicinal product of a vector according to the invention in which the oligonucleotide is transcribed to an "antisense" RNA molecule or a ribozymic RNA molecule which blocks the expression of a gene involved in a pathology, by hybridizing with and, where appropriate, cutting its messenger RNA of cellular, viral, bacterial or parasitic origin.

The medicinal product according to the invention may be used as an antiviral antitumor, antibiotic or antiparasitic agent, or in any pathology in which a gene is abnormally expressed, either through mutation or through deregulation.

The subject of the present invention is also a method for blocking the expression of a gene in vivo using a vector according to the invention in which said oligonucleotide is transcribed to an antisense or ribozymic RNA molecule which hybridizes with or, respectively, cuts the messenger RNA of said gene.

The subject of the present invention is also a method for the treatment of cells ex vivo using a vector according to the invention.

In its in vivo or ex vivo therapeutic applications, it is entirely appropriate to use a viral or retroviral vector which enters the cell by transfection or infection. In particular, as a medicinal product according to the invention, a vector is used consisting of a defective viral vector such as an adenovirus or a defective retroviral vector such as a murine retrovirus.

In effect, the vector used to convey the gene construction according to the invention to its theoretical target can be a retroviral vector with transport of the recombinant construction by a borrower capsid and insertion of the genetic material into the DNA of the host cell.

Techniques that consist in using vectors, in particular viral vectors (retroviruses, adenoviruses, adeno-associated viruses), to transport genetic material and make it enter target cells and to introduce genetic modifications effectively into various somatic tissues such as muscle, liver, brain and hematopoietic cells are known to persons skilled in the art. In particular, hematopoietic tissue (leukocytes, red cells, platelets, etc.) exhibits two essential features which make this tissue a good candidate for the approaches of gene therapy:

the blood cells can be readily removed without traumatizing the patient. Furthermore, the conditions of culture of these cells (use of various cytokines) have become refined and permit ex vivo maintenance for variable time periods (freeing, culture).

study of the differentiation of the various lines of which the hematopoietic system is composed has enabled it to be shown that all of these lines are derived from a common progenitor (Uchida N., Fleming W. H., Alpern E. J. and Weissman I. L. 1993 Current Opinion in Immunology, 5, 177–184). This makes it possible to introduce the desired genetic modification into stem cells which, after reimplantation, are capable of recolonizing the entire hematopoietic tissue.

Characterization of the precursor cells has enabled it to be established that the presence of a surface protein (CD34) enables them to be distinguished from other cell types as being CD34+ cells.

At all stages of differentiation, hematopoietic cells proliferate. As a result, the introduction of forcing genes into these cells makes it obligatory not to "dilute" the gene during successive cell divisions. Retroviruses, which integrate permanently into the genome of the recipient cell and for which the molecular mechanism of replication is relatively well known, are seen to be good candidates for the gene therapy of hematopoietic cells.

The use of retroviral vectors to transport genetic material necessitates, on the one hand carrying out the genetic construction of the recombinant retrovirus, and on the other hand having a cell system available which provides for the function of encapsidation of the genetic material to be transported:

in a first stage, genetic engineering techniques enable the genome of a murine retrovirus such as Moloney virus (murine retrovirus belonging to the murine leukemia virus group: Reddy E. P., Smith M. J. and Aaronson S. A., 1981, Science. 214, 445–450) to be modified. The retroviral genome is cloned into a plasmid vector, from which all the viral sequences coding for the structural proteins (genes: Gag, Env) as well as the sequence coding for the enzymatic activities (gene: Pol) are then deleted. As a result, only the necessary sequences "in cis" for replication, transcription and integration are retained (sequences corresponding to the two LTR regions, encapsidation signal and primer binding signal). The deleted genetic sequences may be replaced by non-viral genes such as the gene for resistance to neomycin (selection antibiotic for eukaryotic cells) and by the gene to be transported by the retroviral vector.

in a second stage, the plasmid construction thereby obtained is introduced by transfection into the encapsidation cells. These cells constitutively express the Gag, Pol and Env viral proteins, but the RNA coding for these proteins lacks the signals needed for its encapsidation. As a result, the RNA cannot be encapsidated and enable viral particles to be formed. Only the recombinant RNA emanating from the transfected retroviral construction is equipped with the encapsidation signal and is encapsidated. The retroviral particles produced by this system contain all the elements needed for the infection of the target cells (such as CD34+ cells) and for the permanent integration of the gene of interest into these cells. The absence of the Gag, Pol and Env genes prevents the system from continuing to propagate.

According to the present invention, the VA-antisense genes have the property of being transcribed by RNA polymerase III. This feature has led to the development of two types of retroviral constructions in which the VA-antirev genes have been cloned as described in Example 6.

DNA viruses such as adenoviruses can also be suited to this approach although, in this case, maintenance of the DNA in the episomal state in the form of an autonomous replicon is the most likely situation.

It is self-evident that the use of a viral vector, originating from an adenovirus, is especially suitable when the viral gene is an adenovirus gene. Adenoviruses possess some advantageous properties. In particular, they have a fairly broad host range, are capable of infecting quiescent cells and do not integrate into the genome of the infected cell. For these reasons, adenoviruses have already been used for the transfer of genes in vivo. To this end, various vectors derived from adenoviruses have been prepared, incorporating different genes (beta-gal, OTC, alpha-1At, cytokines, etc). To limit the risks of multiplication and the formation of infectious particles in vivo, the adenoviruses used are generally modified so as to render them incapable of replication in the infected cell. Thus, the adenoviruses used generally have the E1 (E1a and/or E1b) and possibly E3 regions deleted.

The defective recombinant adenoviruses according to the invention may be prepared by any technique known to persons skilled in the art (Levrero et al., Gene 101 (1991) 195, EP 185,573; Graham, EMBO J. 3 (1984) 2917). In particular, they may be prepared by homologous recombination between an adenovirus and a plasmid in a suitable cell line. The cell line used should preferably (i) be transformable by said elements, and (ii) contain the sequences capable of complementing the portion of the genome of the defective adenovirus, preferably in integrated form in order to avoid risks of recombination. As an example of a line, the human embryonic kidney line 293 (Graham et al., J. Gen. Virol 36 (1977) 59) which contains, in particular, integrated in its genome, the left-hand portion of the genome of an adenovirus Ad5 (12%), may be mentioned.

The adenoviruses which have multiplied are thereafter recovered and purified according to standard techniques of molecular biology.

According to the present invention, an exogenous DNA sequence coding, in particular, for an antisense RNA is inserted into the genome of the defective recombinant adenovirus at the place where the VA gene is located.

Pharmaceutical compositions comprising one or more viral vectors, such as defective recombinants as described above, may be formulated for the purpose of topical, oral, parenteral, intranasal, intravenous, intramuscular, subcutaneous, intraocular, and the like, administration. Preferably, they contain vehicles which are pharmaceutically acceptable for an injectable formulation. These can be, in particular, isotonic, sterile saline solutions (of monosodium or disodium phosphate, sodium, potassium, calcium or magnesium chloride, and the like, or mixtures of such slats), or dry, in particular lyophilized, compositions which, on addition, as appropriate, of sterilized water or of physiological saline, enable particular injectable solutions to be made up.

The doses of defective recombinant virus used for the injection may be adapted in accordance with various parameters, and in particular in accordance with the mode of administration used, the pathology in question, the gene to be expressed or the desired duration of treatment. Generally speaking, the recombinant adenoviruses according to the invention may be formulated and administered in the form of doses of between $10^4$ and $10^{14}$ pfu/ml, and preferably $10^6$ to $10^{10}$ pfu/ml. The term pfu ("plaque forming unit") corresponds to the infectious power of a solution of virus, and is determined by infection of a suitable cell culture and measurement, generally after 48 hours, of the number of plaques of infected cells. The techniques of determination of the pfu titer of a viral solution are well documented in the literature.

The use of genetically modified viruses as a shuttle system for transporting the modified genetic material not only enables the genetic material to be made to enter the recipient cell by the expedient of using a borrower viral capsid, but also enables a large number of cells to be treated simultaneously and over a short period of time; this opens the way to curative approaches directed in vitro at cells already infected with the virus to be inhibited, but also permits therapeutic treatment applied to the whole body.

According to the invention, it is possible to use viral trans-activators. In particular, the E1a protein of adenovirus stimulates the transcriptional activity of polymerase III (23), in particular by mobilizing the limiting TFIIIC factor. This potentiating effect of polymerase III is most particularly observed if the DNA carrying the VA gene is in episomal form (frequently the case for adenoviruses). It is possible to use this property of the E1a protein to stimulate the efficacy of the "VA-RNA polymerase III" system, most particularly during transitory expression experiments, either with E1a gene cloned in cis to the VA RNA gene, or in trans by cotransfection.

In addition, the Tat protein of HIV could stimulate the transcriptional activity of polymerase III.

The use of viral trans-activators coupled with the vectorizing of the antisense molecule may be turned to good account according to the invention as regards specificity of action with respect to cells infected with HIV (or other pathogenic virsues). Two complementary strategies may be applied:

with the object of conferring "cellular immunity" on cells which are permissive to HIV infection (CD4+), the treatment is carried out "ex vivo" by removing stem cells emanating from the marrow, sorting them and modifying them genetically "ex vivo";

a "curative" strategy is also possible, by means of instituting a dependence of the replication of the vector on the presence of the Tat protein of HIV. This dependence allows the vector to replicate effectively only i cells infected with the virus.

The preparation and development of antisense cassettes according to the invention, which can be adapted to many research topics, are envisaged in a very large number of fields including, in particular, molecular oncology and cellular determination.

Other features and advantages of the present invention will become apparent in the light of the detailed description of the embodiment which follows.

BRIEF DESCRIPTION OF THE DRAWINGS

FIG. 1 shows the nucleotide sequence of the adenovirus 2 VAI gene (SEQ ID NO: 1).

| | |
|---|---|
| XXXXXX | VAI RNA gene (Transcribed region) |
| XXXXXX | Oligonucleotides at the 5' and 3' ends of the VAI gene, serving as primers for PCR |
| XXXXXX | Sequences of Boxes A and B needed for transcription of the VAI RNA gene by polymerase III |
| XXXXXX | Insertion site of exogenous sequences |

Figure 2:
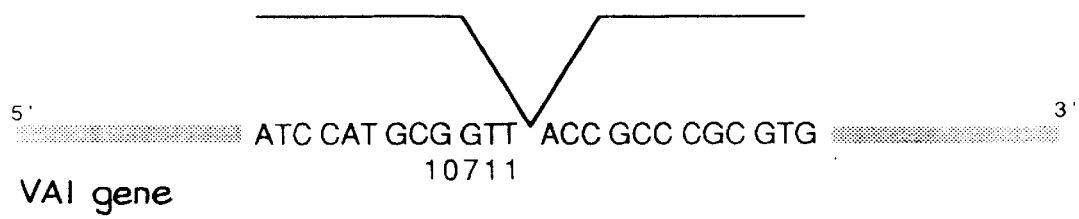

FIG. 2 shows antisense (SEQ ID NO: 2 and 3) and random sequences (SEQ ID NO: 4) inserted at necleotide 10711 (SEQ ID NO: 5) of the VAI gene.

Figure 3:
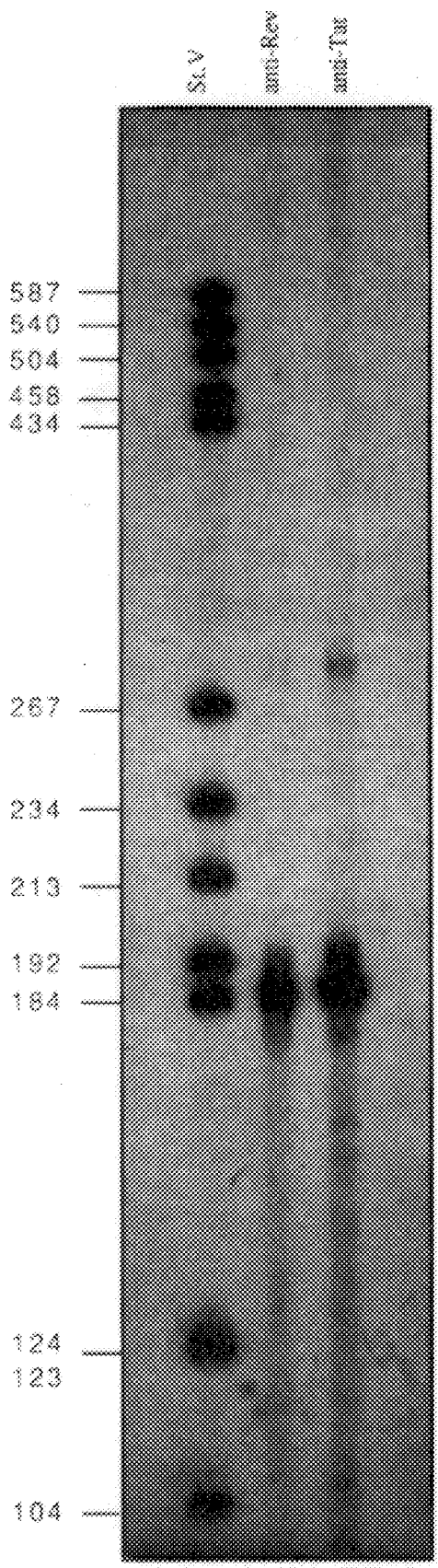

FIG. 3 shows the urea/acrylamide gel analysis of the products of acellular transcription of the PVV2/VAI/antisense constructions.

Figure 4:
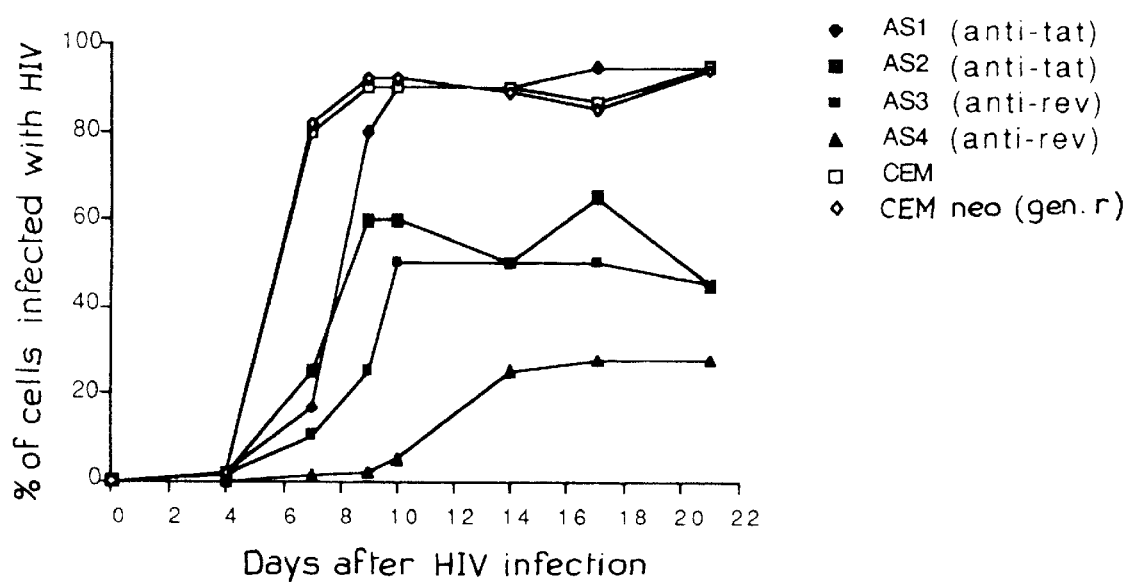

FIG. 4 shows the kinetics of HIV infection of CEM transfected or otherwise with an antisense construction.

Figure 5:
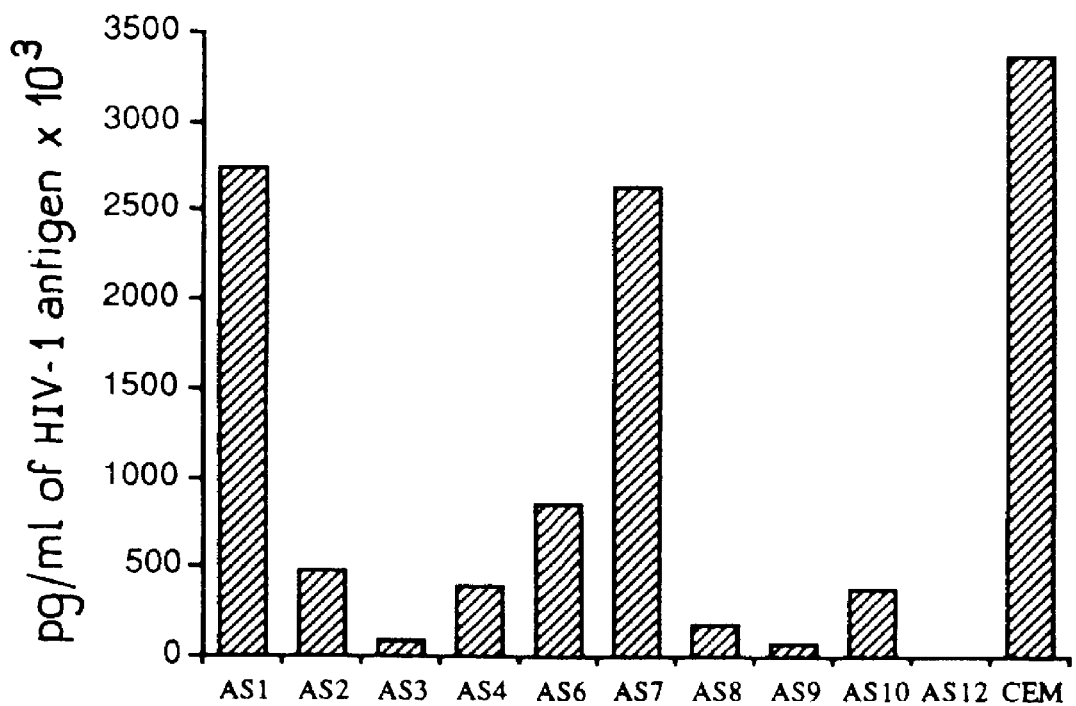

FIG. 5 shows the assay of HIV antigens present in the supernatants of CEM cells transfected with antisense constructions.

The assays of HIV antigens were performed 5 hours after renewal of the culture supernatant and 24 days after the beginning of the infection.

Secondary structures of the VA RNAs: the VAI RNA structure (A) and two possible structures for the VAII RNAs (B and C) are described in Reference 13.

Figure 6:
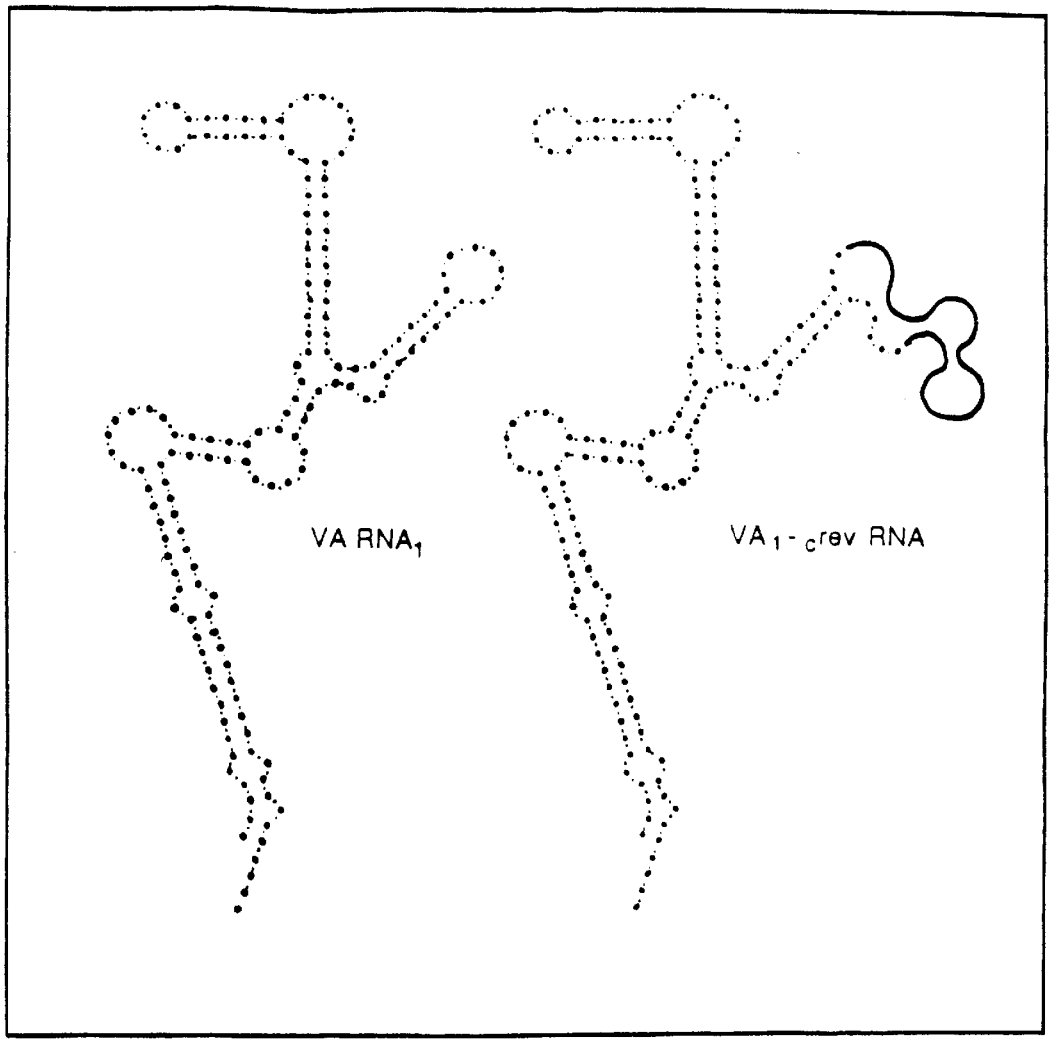

FIG. 6 shows the secondary structure of the VAI gene.

FIG. 7 shows the scheme for insertion of an oligonucleotide by the "overlap" PCR method.

FIG. 8 shows the expression of the VA-antisense construction in the AS10 population lane a: RNA of cells of the AS10 population lane b: RNA of cells of the HepG$_2$ line infected with type 2 adenovirus.

FIG. 9 presents results of Northern blotting of the RNAs transcribed from a plasmid carrying the VA-anti-rev and VA-anti-tat genes obtained in Example 5 with the construction carrying the rev gene and the tat gene.

FIG. 10 shows the construction of the retroviral vectors I and II derived from the vector pMV7 of Example 6.

Figure 11:
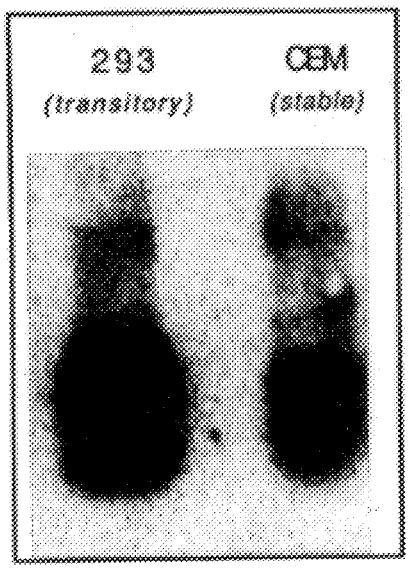

FIG. 11 shows the transitory expression of the modified VAI genes of Example 7 in 293 cells.

EXAMPLE 1

Cloning of the VAI Gene

The gene chosen for the experiments proposed below is the adenovirus 2 VAI RNA gene. The adenovirus sequence is available in the database: Genbank-ref.: ADBVAI, transcribed sequences from nucleotide 10610 to nucleotide 10769 (FIG. 1 presents the sequence elements in question). The conformation of the RNA in solution has been published and is presented in FIG. 6 (13, 14).

Cloning of the recombinant VAI gene is carried out in a plasmid vector of the PVV2 type (15) carrying in cis the geneticin resistance gene (under the control of the TK promoter) or in a vector replicating autonomously in a eukaryotic system, of the pCEP-4 type (marketed by Invitrogen) or alternatively of the pHEBo type (kindly supplied by R. P. SEKALY, Immunology Laboratory, Montreal). These latter vectors are carriers of the oriP and Ebna-1 regions and they also carry the hygromycin resistance gene (16, 17).

The adenovirus 2 VAI gene was cloned after a PCR amplification step. The oligonucleotides used in this PCR were chosen on the 5' side upstream of the transcription initiation site of the VAI gene, and on the 3' side downstream of the TTTT termination site (FIG. 1). The 5' ends of each oligonucleotide are equipped with the ClaI enzymatic cleavage site, which is a single site in plasmid pVV2, or alternatively the HindIII site for cloning into plasmid pHEBo. Transformation of bacterial with "pVV2-VAI" constructions enabled several recombinant clones to be obtained.

EXAMPLE 2

Insertion and Cloning of Antisense Sequences

For HIV, the oligonucleotide sequence to be inserted was determined initially in accordance with the antisense sequences already published by other authors: anti-rev (18) or anti-tat (19) and random sequence serving as a specific control (see FIG. 2) (the tat and rev proteins are two viral proteins whose regulatory role is critical for replication of the virus).

In investigations currently in progress, use is being made of ribozyme type sequences, with cloning of the recombinants carrying ribozymic sequences published by Goodchild & Kohli in 1991 (20).

The use of "overlap" PCR (see FIG. 7) enabled oligonucleotides of variable size to be inserted into the VAI gene. The antisense "anti-rev", "anti-tat" and "random" sequences were inserted at nucleotide 10711 of the VAI RNA sequence (FIG. 2). The VAI genes thus modified by insertion of the antisense sequence are cloned into the ClaI site of plasmid pVV2 as described above.

The constructions obtained were all sequenced (on 200 nucleotides), and then tested in an acellular transcription system to check the functionality as well as the relative efficacy of transcription of each construction. To produce in vitro transcriptions, the protocol followed is that described by Wu (21) and Weil (22). Briefly, 3 μg of DNA under test are incubated for 90 min at 29° C. in the presence of cell extracts containing polymerase III activity and of nucleotides including, in particular, [alpha-$^{32}$P]-dGTP. After synthesis, the products of the reaction are analyzed on acrylamide gel (FIG. 3 presents the type of results obtained).

The observed sizes correspond well to the expected sizes for each construction, namely: native VAI RNA 160 nucleotides, VAI RNA/anti-rev 188, VAI RNA/anti-tat 190. The other VAI RNA/ribozyme constructions have not yet been analyzed.

It is indeed verified that the insertion of exogenous sequences into the VA gene does not affect its level of transcription by polymerase III.

EXAMPLE 3

Inhibition of Viral Replication

The preparation and development of the antisense tools are carried out, in the case of antiviral antisense sequences, on cell lines which are permissive for replication of the virus under study. For example, for anti-HIV antisense sequences, the CEM or MOLT-4 lympho-blastoid lines, both of which are good producers of viruses, are chosen.

CEM line cells (from which mycoplasmata had been cleared) were transfected with the various recombinant plasmids (pVV2/VAI/anti-rev, pVV2/VAI/anti-tat, pVV2/VAI and pVV2 control). The cell transfection techniques used depend on the cell model under study.

For cells in suspension, electroporation was preferably used (apparatus of the Gene Pulser$^{(R)}$ type, Biorad; the electric shocks are produced at 200 V and 960 µF).

After transfection, transduced cells are distributed in 96 independent culture wells and selected by the action of the antibiotics geneticin 1.5 mg/ml (plasmid pVV2 ) or hygromycin 400 µg/ml (plasmid PHEBo). Maintenance of the selection pressure remains necessary throughout the experiments. To day, using electroporation, the CEM line has been transfected with recombinant constructions of plasmid pVV2/anti-rev, pVV2/anti-tat, pVV2/VAI and pVV2.

Geneticin-resistant, non-clonal cell populations emanating from different culture wells are selected on the basis of good cell multiplication with a low mortality rate. The cell populations emanating from transfection with "antisense" plasmids are numbered AS index X (AS: AntiSense, X no. of the selection well).

Each population is infected with infectious supernatant originating from cells chronically infected with HIV virus (particle-rich supernatant); the strain used does not exhibit a cytopathic effect on the cells used (strain LAV/BRU, JC Cherman, Marseilles). The kinetics of viral replication show that, under the usual conditions, more than 95% of the CEM produce viral particles 7 to 8 days after infection (FIG. 4).

The measurement of viral replication is estimated by indirect immunofluorescence. Briefly, 5000 cells are fixed on glass slides and incubated for 30 min in the presence of an anti-HIV serum originating from an HIV-positive patient and diluted to ¹⁄₄₀. Visualization is accomplished using a second antibody, specific for human immunoglobulins, conjugated to fluorescein isothiocyanate (FITC).

Viral replication may also be measured by assaying the concentration of HIV-I antigens present in the culture supernatant (assay carried out with the ABBOT HIVAG-1$^{(R)}$ kit. The kinetics of infection are produced simultaneously on the cells transfected with the various plasmids and emanating from the selection with geneticin.

FIG. 4 presents the results obtained on infecting, in a comparative manner, the CEM line serving as a positive control, the geneticin-resistant CEM line (CEM.gen.r.) transfected with PVV2, 2 "anti-tat" population (AS1 and AS2) and 2 "anti-rev" populations (AS3 and AS4). Measurement of the viral replication was monitored by observing and counting the number of HIV-positive cells detected by indirect immunofluorescence at different days after infection:

Superposition of the "CEM" and "CEM.gen.r." curves shows that the presence of geneticin in the medium does not affect the infection of the CEM cells by the HIV virus. It is apparent that the 4 "antisens" populations tested exhibit a significant delay in starting the infection; the eclipse period is extended by 2 days for AS1 and up to 6 days in the case of AS3. Furthermore, a small percentage of cells are infected in the case of certain lines (AS2, AS3, AS4) (25 to 60%), even at a late stage after infection, reflecting the resistance to viral infection of a large number of cells within these uncloned populations. This does not apply to the AS1 line, which exhibits more than 95% of positive cells 10 days after the beginning of the infection.

FIG. 5 presents the results obtained during an experiment of the same type, but carried out with a broader panel of ASX populations and quantified by measurement of the HIV-1 antigens present it the supernatants at various days after infection with HIV. Only the results obtained on day 24 are presented (these being representative of the results obtained on the other days). In order to avoid the accumulation of viral particles and a distortion of the comparative measurements, the supernatants are collected 5 hours after changing the previous medium.

The "VAI/anti-tat" populations correspond to the AS1, AS2, AS6, AS7 and AS8 conditions, and the "VAI/anti-rev" populations to the AS3, AS4, AS9, AS10 and AS12 conditions.

It is apparent that most of the "antisense" populations exhibit a significant decrease in the quantity of HIV-1 antigens measured in the supernatants; for 8 lines out of 10 (AS2, AS3, AS4, AS6, AS8, AS9, AS10 and AS12), a less than 20% production of viral antigens is measured in comparison with the control, and 2 populations reach 70% of the control level (AS1 and AS7).

The results obtained for the AS1,2,3 and AS4 populations according to 2 techniques of measurement of viral replication, mainly immunofluorescence (FIG. 4) and antigen concentrations (FIG. 5), are concordant. In FIGS. 4 and 5, the AS1, AS2, AS3 and AS4 populations are identical.

EXAMPLE 4

Measurement of the Level of Expression of VAI RNA

It is possible to characterize the expression of antisense RNAs by means of Northern blotting techniques or alternatively techniques of hybridization in a liquid medium. The RNAs are prepared according to the following protocol: 25×10⁶ cells are rinsed twice with saline buffer, and the cells are lysed at 4° C. by hypotonic shock (10 mM Tris pH 7.4, 10 mM NaCl, 3 mM MgCl$_2$) and by the action of 1% NP 40; after centrifugation (10,000 rpm, 10 minutes) the supernatant containing the cytoplasmic RNAs is cleared of residual proteins by 3 phenol-chloroform extractions ad the RNAs are concentrated with ethanol. 10 µg of RNA are analyzed by Norther blotting and hybridized with a single-stranded probe specific for the 3' region of the VA gene. The results obtained are presented in FIG. 8. The results presented here illustrate the fact that, in vivo, the constructions tested (in this case AS10, "VA/anti-rev") are expressed and that the transcription product obtained is indeed of the expected size.

EXAMPLE 5

Simultaneous Use of Several Chimeric VA Genes: "Antisense Cocktails"

A genetic construction was made containing the succession of the two genes VA-anti-rev and VA-anti-tat, cloned into the ClaI and HindIII sites, respectively, of plasmid pVV2. Acellular transcription experiments carried out with this construction demonstrated that each of these genes was expressed correctly:

The RNAs emanating from transcription in an acellular system of the plasmid carrying the two genes were analyzed by Northern blotting and visualized either with a probe specific for the rev sequence or with a probe specific for the tat sequence. The results obtained are presented in FIG. 9.

The protocol for acellular transcription is that already used in Example 2 and for FIG. 3 (Ref. 21 Wu et al., and 22 Weil et al.).

Northern-blot analysis of the RNAs is carried out after purification of the RNAs/treatment with DNase I and then proteinase K and phenol-chloroform extraction), separation on agarose gel in a denaturing medium, transfer onto membrane and visualization either with the rev probe (lane a) or with the tat probe (lane b).

EXAMPLE 6

Vectorizing of the VA-Antisense Genes with Modified Murine Retroviruses-Transfer to Progenitors of Hematopoietic Cells.

1) Type I retroviral vector:

The vector used is plasmid pMV7 (P. T. Kirschmeier, G. M. Housey, M. D. Johnson, A. S. Perkins and I. B. Weinstein, 1988, DNA, Vol. 7, 3, 219–225). It is composed, on the one hand, of the sequences needed for plasmid maintenance, and on the other hand of the two LTRs of Moloney virus flanking the neomycin resistance gene (under the control of the TK promoter). The HindIII, ClaI and EcoRI cloning sites situated between the 5' LTR and the neomycin gene permit the insertion of exogenous sequences. The encapsidation cell is the DAMP cell (R. Mann, R. C. Mulligan and D. Baltimore, 1983, Cell, 33, 143–159). The genetic constructions were cloned at the HindIII site of PMV7 and the recombinant plasmids obtained were transfected into DAMP cells. DAMP cells which had become neomycin-resistant were subcloned. Clones exhibiting a strong infectious power, detected in the culture supernatants, were selected. These clones enabled CEM line lymphocytes (T4-helper lymphocytes) to be infected. Infection is carried out by means of an overnight coculture between the DAMP cells and the lymphocytes. Lymphocytes which have been infected have become, in turn, neomycin-resistant and can thus be selected. The RNAs originating from these lymphocytes were analyzed and the expression of the VA-anti-rev gene (carried by the integrated proviral sequence) was detected.

However, the possible interference between the activity of RNA polymerase II, which transcribes the whole of the viral genome from the 5' LTR, and the RNA polymerase III activity might in some cases prove to be a factor adversely affecting the efficacy of such a system.

2) Type II retroviral vectors:

The enhancer signals present in the U3 region of the 3' LTR of the Moloney virus cloned into pMV7 were deleted, and these signals were replaced by single-cloning sites in this plasmid (these modifications being carried out by means of PCR technology). The antisense constructions are inserted at these sites. This modification has two advantages: on the one hand it enables the cloned gene to be duplicated as a result of the action of reverse transcription (the U3 region present in each of the two LTRs originates from the U3 region situated in the LTR at the 3' end of the preceding provirus), but, most particularly, this no longer permits the RNA polymerase II to transcribe the provirus integrated in the recipient cell. This avoids the interference with the RNA polymerase III and provides for safe functioning with respect to the activation of adjacent genes, which is always a possibility.

More specifically, the vector II was obtained as illustrated in FIG. 10:

1) the single HindIII site has been deleted (cleavage, filling in with DNA polymerase, relegation).
2) complete digestion of PMV7 with ClaI liberates the selectable gene (neomycin), and the resulting plasmid portion is then treated partially with the enzyme Xho I. Only the fragment containing the 5' LTR is purified on agarose gel (5064 bp). As a result, the 3' LTR is lost.
3) the 3' LTR is then replaced by a modified 3' LTR for which the enhancer regions situated in the U3 region have been deleted and replaced by a HindIII site (this is carried out by means of PCR technology).
4) the antisense gene has been cloned into the newly created HindIII site.
5) this new retroviral construction may be used in the usual manner:
   transfection in encapsidation cells (CRIP cells, ref. Danos and R. C. Mulligan, Proc. Natl. Acad. Sci., 1988, vol. 85, 6460–6446).
   recovery of the supernatants with estimation of the infectious titer.
   these recombinant retroviral particles will be used to transduce the target cells.

With the object of avoiding the production of wild-type recombinant particles of Moloney virus, the DAMP encapsidation cell is changed in favor of the CRIP cell (O. Danos and R. C. Mulligan, Proc. Natl. Acad. Sci., 1988, 85, 6460–6446) The CRIP cell contains two auxiliary retroviral genomes from which the 3' LTR end and the encapsidation signal have been deleted and which are mutated, one in the Gag region and the other in the env region.

By complementation, the production of Ga, Pol and Env proteins is effected, but the provability of obtaining wild-type genomes obtained by recombination is reduced to zero. The collective improvements proposed and described here make it possible to provide for the production of recombinant retroviral particles carrying one or more VA/antisense (pMV/AS) genes correctly transcribed by polymerase III. This vector also affords optimal safety of functioning for the purpose of the therapeutic applications envisaged.

EXAMPLE 7

Transitory Expression of VA-Antisense Genes

With a view to a localized, short-term therapy, the transitory expression of the VA-antisense genes was verified in a cellular system. In transitory expression, the VA-antisense gee is not integrated into the genome of the host cell and accumulates in large amounts in the nucleus, where it is transcribed.

Adherent cells (line 293: human kidney embryonic cells) were transfected with 20 g of the anti-rev pVA plasmid. The technique used is calcium phosphate transfection. This technique consists in brining the calcium phosphate-precipitated plasmid DNA and the cells into contact for 18 hours while increasing the absorption of DNA on the cell membranes and limiting the action of cellular DNases on the entering DNA. The RNAs are prepared 48 hours after transfection, as described above, and analyzed by Norther blotting with a probe specific for anti-rev VA RNAs. FIG. 11 shows a stronger transitory expression of the RNAs (lane 293) in comparison with the RNAs produced in the cells which express the integrated VA RNA in a stable manner (lane CEM).

REFERENCES

1. Weintraub H., Les ADN et les ARN antisens., (Antisense DNAs and RNAs), (1990), Pour la science, 149: 54–61.

2. Melton D. A., Injected anti-sense RNAs specifically block messenger RNA translation in vivo., (1985), Proc. Natl. Acad. Sci. USA., 82, 144–148.

3. Geiduschek E. P., Tocchini-Valentini G. P., Transcription by polymerase III, (1988), Ann. Rev. Biochem, 57, 873–914.

4. Galli G., Hofstetter H., Birnstiel M. L., Two conserved sequence blocks within eukaryotic tRNA genes are major promoter elements., (1981), Nature 294, 626–631.

5. Cotten M., Birnstiel M. L. Ribozyme mediated destruction of RNA in vivo., (1989), EMBP J., 8, 3861–3866.

6. Vasseur M., Les virus oncogenes., (Oncogenic viruses), (1989), Herman eds., Adenovirus, 151–184.

7. Furtado M. R., Subramanian S., Bhat R. A., Fowlkes D. M., Safer B., Thimmappaya B., Functional dissection of Adenovirus VAI RNA (1989), J. Virol., 63, 3423–3434.

8. Thimmappaya B., Weinberger C., Schneider R. J., Shenk T., Adenovirus VAI RNA is required for efficient translation of viral mRNAs at late time after infection., (1982), Cell, 31, 543–551.

9. Akusjärvi G., Svensson C., Nygard O., A mechanism by which adenovirus-associated RNAI controls translation in a transient expression assay., (1987), Mol. Cell. Biol., 7, 549–551.

10. Mellits K. H., Kostura M., Matthews M. B., Interaction of Adenovirus VA RNA with the protein kinase DAI: Non equivalence of Binding and function., (1990), Cell, 61, 812–815.

11. Ghadge G. D., Swaminanthan S., Katze M. G., Thimmappaya B., Binding of the adenovirus VAI RNA to the interferon-induced 68kDa protein kinase correlates with function., (1991), Proc. Natl. Acad. Sci. USA, 88, 7140–7144.

12. Jennings P. A., Molloy P. L., Inhibition of SV40 replicon function by engineered antisense RNA transcribed by RNA polymerase III., (1987), EMBO J., 6/3, 3043–3047.

13. Akusjärvi G., Mathews M. B., Andersson P., Vennstrom B., Petterson U., Structure of genes for virus-associated RNA1 and RNA2 of adenovirus type 2., (1980), Proc. Natl. Acad. Sci. USA, 77/5, 2424–2428.

14. Monstein H. J., Philipson L., The conformation of adenovirus VAI RNA in solution, (1981), Nucleic Acids Res., 9, 4239–4250.

15. Meneguzzi G., Binétruy B., Grisoni M., Cuzin F., Plasmidial maintenance in rodent figroblasts of BPVI-pBR322 suttle vector without immediately apparent ongogenic transformation of the recipient cells (1984), EMBO J., 3, 112–116

16. Hambor J. E., Hauer C. A., Shu H. K. Groger R. K., Kaplan D. R., Tikoncinski M. L., Use of an Epstein Barr virus episomal replicon for anti-sense RNA-mediated gene in a human cytotoxic T cell-clone., (1989), Proc. Natl. Acad. Sci. USA, 85, 4010–4014.

17. Yates J. L., Warren N. Sugden B., Stable replication of plasmids derived from Epstein Barr virus in various mammalians cells., (1985), Nature, 313, 812–815.

18. Matsukura M., Zon G., Shinozuka K. Robert-Guroff M., Shimade T., Stein C. A., Mitsuya H., Wong-Staal F., Cohen J. S. Broder S., Regulation of viral expression of human immunodeficiency virus in vitro by an antisense phosphorothioate oligodeoxynucleotide against rev (art/trs) in chronically infected cells., (1989), Proc. Natl. Acad. Sci. USA, 86, 4244–4248.

19. Rhodes A., James W., Inhibition of human immunodeficiency virus replication in cell culture by endogenously synthesized antisense RNA., (1990), J. Gen. Virol., 71, 1965–1974.

20. Sarver N., Cantin E. N., Chang P. S., Zaia J. A., Ladne P. L., Stephens D. A., Rossi J. J., Ribozymes as potential anti-HIV-1 therapeutic agents., (1990), Science, 247, 1222–1225.

21. Wu G. -J., Zubay G., Prolonged transcription in a cell-free system involving nuclei and cytoplasm (1974), Proc. Natl. Acad. Scie. USA, 71, 1803–1807.

22. Weil A. A., Segall J., Harris B., Ng S. -Y., Roeder R. G., Faithful transcription of eucaryotic genes by RNA polymerase III in systems reconstituted with purified DNA templates., (1979), J. Biol. Chem., 254, 6163–6173.

23. Hoeffler W. K., Roeder R. G., Enhancement of RNA polymerase III transcription by the Ela gene product of adenovirus, (1985), Cell., 41, 955–963.

24. Chomczyski P., Sacchi N., Single-Step Method of RNA isolation by Acid Guanidinium Thiocyanate-Phenol-Chloroform Extraction, (1987), Analytical Biochem., 162, 955–963.

25. Haseloff J., Gerlach W. L., Simple RNA enzymes with new and highly specific endoribonuclease activities, (1988), Nature, 334, 585–591.

26. Hambor J. E., Hauer C. A., Shu H. K., Groger R. K., Kaplan D. R., Tykocinski M. L., (1988), Proc. Natl. Acad. Sci. USA, 85, 4010–4014.

27. Aufiero B., Schneider R. J., The hepatitis B virsu X-gene product trans-activates both RNA polymerase II and III promoters, (1990), EMBO J., 9, 497–504.

28. Danos O., Mulligan R., Safe and efficient generation of recombinant retroviruses with amphitropic and ectotropic host ranges, (1988), Proc. Natl. Acad. Sci. USA, 85, 6460–6464.

29. Lévy J. P., Traitements du SIDA: recherche de nouveaux médicatmens et élaboration de thérapies géniques (Treatments for Aids: search for new drugs and development of gene therapies), (1991), médecine/sciences, 7, 830–841.

We claim:

1. A recombinant DNA vector containing a cassette for transcription by RNA polymerase III, comprising an adenovirus VA gene transcribed by RNA polymerase III into which a DNA oligonucleotide has been inserted between or outside the bosses A and B constituting the promoter of said VA gene, wherein the secondary structure of the adenovirus VA gene is maintained and the functionality of the VA gene is maintained except that it is inactivated as regards inhibition of interferon action.

2. The vector as claimed in claim 1, wherein the VA gene is the adenovirus VAI or VAII gene.

3. The vector as claimed in claim 1, wherein the vector is a plasmid or episomal replicative vector or a viral vector.

4. The vector as claimed in claim 1, wherein the adenovirus VA gene is inactivated, by deletion or mutation, as regards inhibition of interferon action.

5. The vector as claimed in claim 1, wherein the oligonucleotide is inserted within the region responsible for the activity of inhibition of interferon action.

6. A vector according to claim 1, which is a defective recombinant adenovirus.

7. A cell infected or transfected with a vector as claimed in claim 1.

8. A method for the intracellular production of an RNA fragment in vitro, in which eucaryotic cells containing RNA polymerase III are transfected or infected with a vector as claimed in claim 1, containing as oligonucleotides a DNA fragment corresponding to the reverse transcript of said RNA and culturing said cells so as to produce said RNA fragment.

9. A method of expressing a DNA oligonucleotide in vitro comprising:
 a. transfecting or infecting a hoist cell with a recombinant vector as claimed in claim 1; and
 b. expressing in the host cell the DNA oligonucleotide inserted into said recombinant vector.

10. A method for the intracellular production of an RNA fragment in vitro, in which eukaryotic cells containing RNA polymerase III are transfected or infected with a vector as claimed in claim 1, containing as oligonucleotides a DNA fragment corresponding to the reverse transcript of said RNA, and in which the eukaryotic cells thus transfected or infected are cultured in a suitable culture medium.

11. The vector as claimed in claim 2, wherein the oligonucleotide is inserted into the intermediate region situated between boxes A and B.

12. The vector as claimed in claim 2, wherein the oligonucleotide contains from 15 to 40 necleotides.

13. The vector as claimed in claim 2, wherein an oligonucleotide is inserted in or in place of the region extending from nucleotide 10694 to 10730.

14. The vector as claimed in claim 2, wherein the oligonucleotide is inserted at nucleotide 10711 of the adenovirus 2 VAI gene shown in FIG. 1.

15. The vector as claimed in claim 2, wherein an oligonucleotide is inserted in the adenovirus 2 VAI gene within one of the following regions:
 a) nucleotides 10635 to 10639;
 b) nucleotides 10682 to 10688;
 c) nucleotides 10733 to 10736;
 d) the VA delta IV gene;
wherein the central region comprising nucleotides 10702 to 10728 has been deleted.

16. The vector as claimed in claim 2, wherein an oligonucleotide is inserted in the adenovirus 2 VAI gene in place of one of the following regions:
 a) nucleotides 10635 to 10639;
 b) nucleotides 10682 to 10688;
 c) nucleotides 10733 to 10736;
wherein the central region comprising nucleotides 10702 to 10728 has been deleted.

17. The vector as claimed in claim 12, wherein the oligonucleotide contains from 15 to 25 nucleotides.

18. The vector as claimed in claim 13, wherein an oligonucleotide is inserted in or in place of the region extending from nucleotide 10702 to 10728.

19. The vector as claimed in claim 15, wherein the oligonucleotide is inserted into the VA delta IV gene.

20. An RNA retroviral vector, which contains an RNA transcript of a recombinant DNA vector containing a cassette for transcription by RNA polymerase III, consisting of an adenovirus VA gene transcribed by RNA polymerase III into which a DNA oligonucleotide has been inserted between or outside the boxes A and B constituting the promoter of said VA gene, wherein the secondary structure of the adenovirus VA gene is maintained and the functionality of the VA gene is maintained except that it is inactivated as regards inhibition of interferon action.

21. A recombinant DNA vector containing a cassette for transcription by RNA polymerase III, wherein the cassette comprises:

(A) a VA gene of adenovirus, wherein the VA gene is transcribable by RNA polymerase III to form an RNA molecule that inhibits interferon-induced protein kinase DAI, wherein said VA gene has a promoter comprises of boxes A and B located in the L1 region of the adenovirus genome; and (B) a DNA sequence comprised of 15 to about 40 nucleotides encoding an antisense molecule or a ribozyme;

wherein the DNA sequence is inserted between or outside boxes A and B of said promoter to thereby inactivate said RNA molecule with regard to inhibition of the interferon-induced protein kinase DAI and further wherein the DNA sequence is under the control of said promoter.

22. The recombinant DNA vector as claimed in claim 21, wherein the adenovirus is adenovirus type 2 and said DNA sequence is inserted between the region of nucleotides 10672 and 10745 of said VA gene.

23. The recombinant DNA vector as claimed in claim 22, wherein said DNA sequence in inserted between the region of nucleotides 10694 to 10730.

24. The recombinant DNA vector as claimed in claim 22, wherein said DNA sequence is inserted between the region of nucleotides 10702 to 10728.

25. The recombinant DNA vector as claimed in claim 22, wherein the vector comprises an autonomously replicating vector, which replicates in a eukaryotic cell.

26. A recombinant DNA vector, wherein the vector comprises:

(A) an autonomously replicating vector, which replicates in a eucaryotic cell;

(B) a VA gene of adenovirus inserted in said vector, wherein the VA gene is transcribable by RNA polymerase III to form an RNA molecule that inhibits interferon-induced protein kinase DAI, wherein said VA gene has a promoter comprised of boxes A and B located in the L1 region of the adenovirus genome; and (C) a DNA sequence comprised of about 15 to about 40 nucleotides encoding an antisense molecule or a ribozyme;

wherein the DNA sequence is inserted between the region of nucleotides 10672 and 10745 of said VA gene between or outside boxes A and B of said promoter to thereby inactivate said RNA molecule with regard to the inhibition of the interferon-induced protein kinase DAI and further wherein the DNA sequence is under the control of said promoter.

27. The recombinant DNA vector as claimed in claim 26, wherein said DNA sequence is inserted between the region of nucleotides 10694 to 10730.

28. The recombinant DNA vector as claimed in claim 26, wherein said DNA sequence in inserted between the region of nucleotides 10702 to 10728.

29. A recombinant DNA vector containing a cassette for the transcription by RNA polymerase III, wherein the cassette comprises:

(A) a VA gene of adenovirus, wherein the VA gene is transcribable by RNA polymerase III to form an RNA molecule that inhibits interferon-induced protein kinase DAI, wherein said VA gene has a promoter comprises of boxes A and B located in the L1 region of the adenovirus genome; and (B) a DNA sequence comprised of 15 to about 40 nucleotides encoding an antisense molecule or a ribozyme;

wherein the DNA sequence is inserted between or outside boxes A and B of said promoter to thereby inactivate said RNA molecule, while maintaining structural topology of the VA gene, and further wherein the DNA sequence is under the control of said promoter.

\* \* \* \* \*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 260 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Adenovirus 2
        ( C ) INDIVIDUAL ISOLATE: VAI gene ( x i ) SEQUENCE DESCRIPTION: SEQ ID NO:1:

```
CGTGCGCAGT  CGTTGACGCT  CTAGACCGTG  CAAAAGGAGA  GCCTGTAAGC  GGGCACTCTT      60
CCGTGGTCTG  GTGGATAAAT  TCGCAAGGGT  ATCATGGCGG  ACGACGGGG   TTCGAACCCC     120
GGATCCGGCC  GTCCGCCGTG  ATCCATGCGG  TTACCGCCCG  CGTGTCGAAC  CCAGGTGTGC     180
GACGTCAGAC  AACGGGGGAG  CGCTCCTTTT  GGCTTCCTTC  CAGGCGCGGC  GGCTGCTGCG     240
CTAGCTTTTT  TGGCCACTGG                                                    260
```

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:2:

```
TGCTCTCCTC  TGTCGAGTAA  AGACAGGATA                                         30
```

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:3:

```
TCGTCGCTGT  CTCCGCTTCT  TCCTGCCA                                           28
```

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
TGCTCTTGTC  CCGTCATCGT  TGCCCCTC                                                28
```

( 2 ) INFORMATION FOR SEQ ID NO:5:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Adenovirus2
    ( C ) INDIVIDUAL ISOLATE: part of VAI gene ( x i ) SEQUENCE DESCRIPTION: SEQ ID NO:5:

```
ATCCATGCGG  TTACCGCCCG  CGTG                                                    24
```